United States Patent [19]
Taheri

[11] Patent Number: 5,843,169
[45] Date of Patent: Dec. 1, 1998

[54] APPARATUS AND METHOD FOR STAPLING GRAFT MATERIAL TO A BLOOD VESSEL WALL WHILE PRESERVING THE PATENCY OF ORIFICES

[76] Inventor: Syde A. Taheri, 268 Dan Troy, Williamsville, N.Y. 14221

[21] Appl. No.: 838,520

[22] Filed: Apr. 8, 1997

[51] Int. Cl.⁶ ..................................................... A61F 2/06
[52] U.S. Cl. ............................ 623/1; 606/108; 606/139; 606/151; 606/153; 604/96
[58] Field of Search ............................. 623/1, 9, 11, 12; 606/139, 108, 151, 153, 192, 194, 195, 219, 191; 604/96, 171; 227/175.1

[56] References Cited

U.S. PATENT DOCUMENTS

| | | | |
|---|---|---|---|
| 4,872,874 | 10/1989 | Taheri | 623/1 |
| 5,104,399 | 4/1992 | Lazarus | 623/1 |
| 5,423,851 | 6/1995 | Samuels | 606/198 |

*Primary Examiner*—Michael Buiz
*Assistant Examiner*—David O. Reip
*Attorney, Agent, or Firm*—Hodgson, Russ, Andrews, Woods & Goodyear LLP

[57] ABSTRACT

The present invention is comprised of an apparatus for stapling graft material to a vessel wall comprising a stapling device, a balloon catheter, a sheath, and an inflation means.

12 Claims, 7 Drawing Sheets

APPARATUS AND METHOD FOR STAPLING GRAFT MATERIAL TO A BLOOD VESSEL WALL WHILE PRESERVING THE PATENCY OF ORIFICES

FIELD OF THE INVENTION

The present invention relates to an apparatus and method for stapling graft material to the aortic wall while preserving patency of orifices of branches of the aorta.

BACKGROUND OF THE INVENTION

Aortic aneurysms, or ruptures, are a very common type of deteriorating disease affecting the ability of a lumen to conduct fluids and in turn may be life threatening. The common repair means is to deploy a graft within the lumen of the affected blood vessel in the region of the aneurysm.

In many cases, however, the repair must take place in the region of orifices of branches of the aorta, such as branches of the thoracic aorta or intercostal arteries. Obviously, when repairing such regions, graft material must be cut away prior to deployment of a graft so that repair may take place while preserving the patency of such orifices. The graft material surrounding the graft opening must then be secured to the blood vessel wall prior to completion of the procedure.

The standard technique for securing graft material around the orifices of branches of the damaged vessel is to make a separate entry into the body in the direct region of the graft opening, then suture the material to the vessel wall.

Several problems are associated with the need for a separate entry. First, the separate entry results in additional scarring, longer post operative recovery time, and natural increased risks associated with multiple entries as compared with a single entry. Second, in the case of engrafting the thoracic aorta while preserving patency of the orifices to branches thereof, utilizing the standard technique requires temporarily tying off the ascending aorta. That step in the repair procedure requires the use of the heart-lung machine. Such bypassing of the heart and lungs carries well known risks of damage to vital organs.

SUMMARY OF THE INVENTION

The present invention is comprised generally of an apparatus and method for stapling graft material to a vessel wall utilizing the same entry point into the vessel as used for initial deployment of the graft while providing substantially unobstructed blood flow during the stapling procedure and preserving the patency of orifices of branches of the vessel. In particular, the apparatus is comprised of a tube, a stapling device, a balloon catheter, and a sheath. The tube comprises a proximal and distal end, an inner and outer surface, and a central lumen. The central lumen contains an opening at the proximal end. The stapling device is integral with the proximal end of the tube and stapling device has an upper, rounded surface and a stapling surface connected to define a substantially hollow center; a substantially hollow center which communicates with the central lumen of the tube. The upper surface of the stapling device is comprised of a stretchable material for enabling a balloon catheter to expand fully within the vessel lumen. The stapling surface contains one or more flexible capsules for temporarily retaining one or more pins, and a conductive wire passes between the inner and outer surfaces of the tube, and continues through the stapling surface and capsules of the stapling device. A magnetic coil is operationally engaged within each capsule and in physical contact with the wire. The balloon catheter contains a balloon at its proximal end which balloon is located within the hollow portion of the stapling device.

The method comprises the steps of: sizing the apparatus with the graft material and the blood vessel; placing the pins within the capsules; covering the apparatus with a sheath; inserting the apparatus into a blood vessel; moving the apparatus to a position of the pins; filling the sheath with fluid if rigidity is needed to pass through regions of the blood vessel; removing the fluid if the blood vessel becomes too narrow to accommodate the enhanced size of the apparatus as filled; applying current to the conductive wire; retracting the sheath; inflating the balloon to a predetermined volume; removing the charge to release the pins; deflating the balloon; and removing the apparatus from the blood vessel.

It is a primary object of the present invention to provide an apparatus and method for stapling graft material to a blood vessel wall.

It is a further object of the present invention to provide an apparatus and method for stapling graft material to a vessel wall while preserving patency of orifices of branches of a blood vessel.

Another object of the present invention is to provide an apparatus and method for stapling graft material to a blood vessel wall without requiring an entry point separate from the entry point for deployment of the graft itself.

It is an additional object of the present invention to provide an apparatus and method which enables substantially unobstructed blood flow during the stapling procedure.

It is yet a further object of the present invention to provide a hydraulic sheath to be used in connection with the stapling apparatus.

DETAILED DESCRIPTION OF THE PREFERRED EMBODIMENTS

Figure 1A:
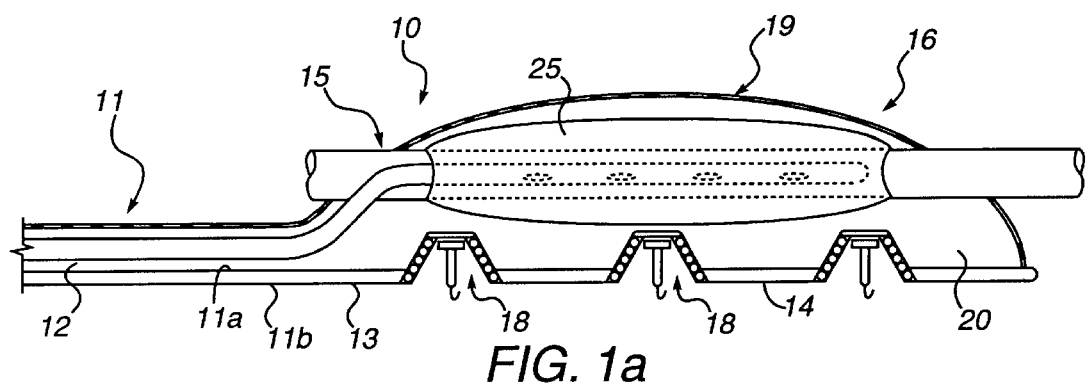
FIG. 1a is a fragmented view of the unsheathed apparatus.

For the purposes of promoting an understanding of the principles of the invention, reference will now be made to the embodiments and methods illustrated in the drawings and specific language will be used to describe the same. It will nevertheless be understood that no limitation of the scope of the invention is thereby intended; such alterations and further modifications in the illustrated devices and methods, and such further applications of the principles of the invention as illustrated therein being contemplated as would normally occur to one skilled in the art in which the invention relates.

Figure 1B:
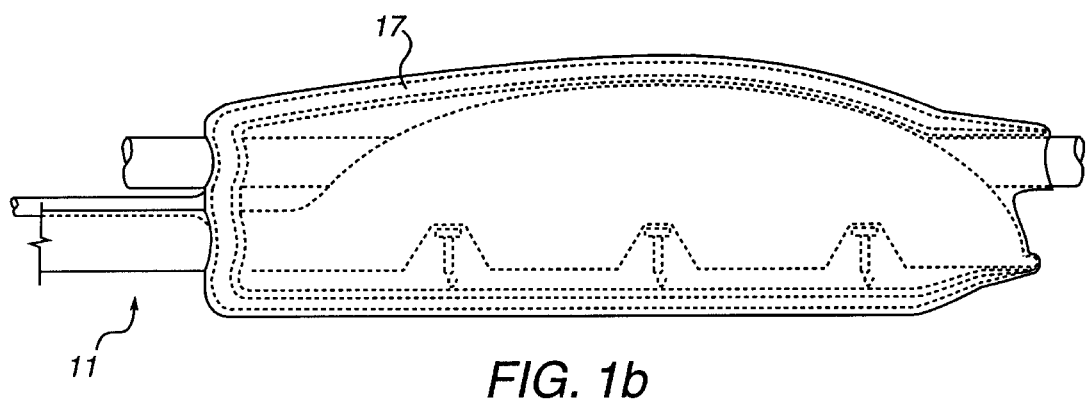
FIG. 1b is a side perspective view of the sheathed apparatus.
Figure 1C:
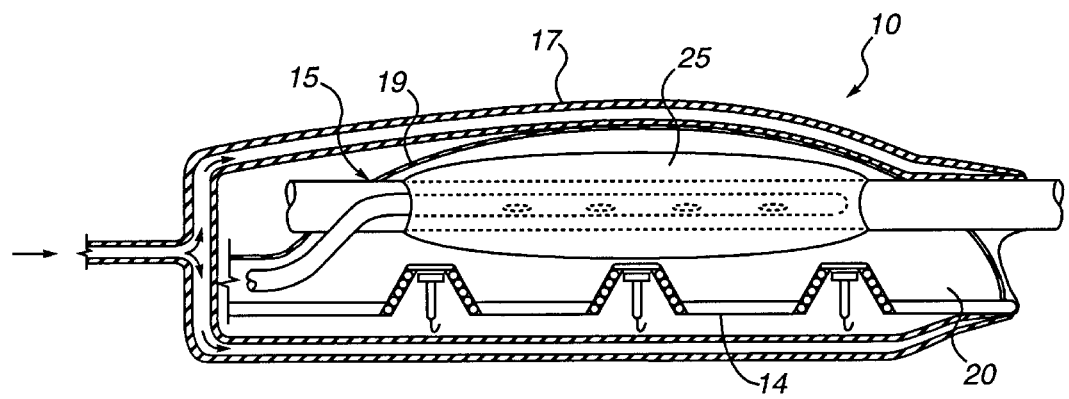
FIG. 1c is a fragmented view of the sheathed apparatus.

As shown in FIGS. 1a–1c, apparatus 10 is comprised generally of tube 11, stapling device 16, balloon catheter 15, and sheath 17.

Tube 11 is preferably comprised of silicone, polyethylene, polyurethane, or other similar material. Tube 11 contains central lumen 12, a proximal end 13, inner surface 11a, and outer surface 11b.

Stapling portion 16 is comprised generally of a stapling surface 14, an upper surface 19 and a substantially hollow interior portion 20 which is in communication with central lumen 12 of tube 11. Moreover, stapling surface 14 is comprised of a plurality of capsules 18, preferably substantially U-shaped, extending into hollow interior portion 20 in their pre-flexed position. The positioning of capsules 18 upon stapling surface 14 is determined by location of branches of the aorta in the region of a deployed graft.

Figure 2:
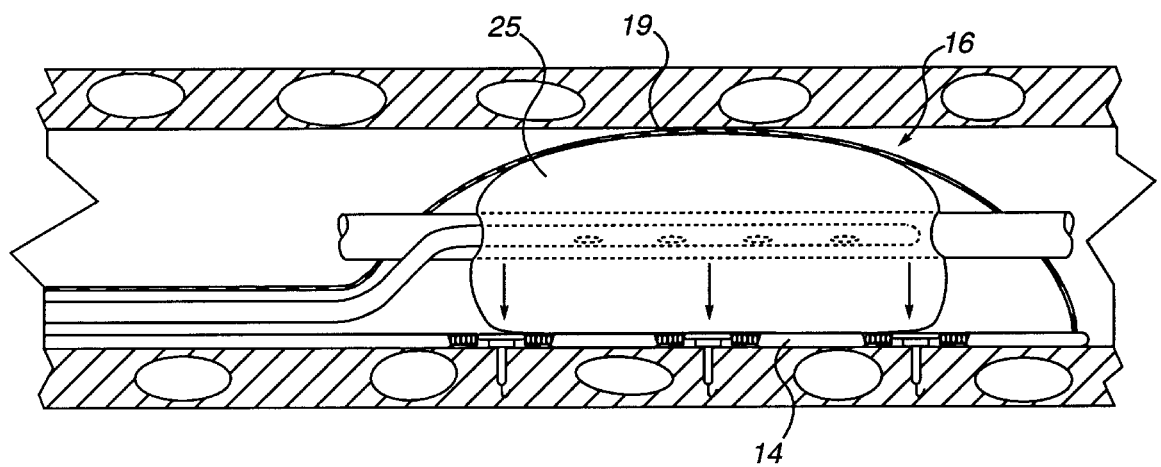
FIG. 2 is a fragmented view of the unsheathed apparatus with an inflated balloon within a blood vessel.

As shown in FIG. 2, upper surface 19 and stapling surface 14 of stapling device 16 are preferably comprised of preferably a flexible polyurethane or silicone rubber material for flexibility during inflation of balloon 25.

Figure 3A:
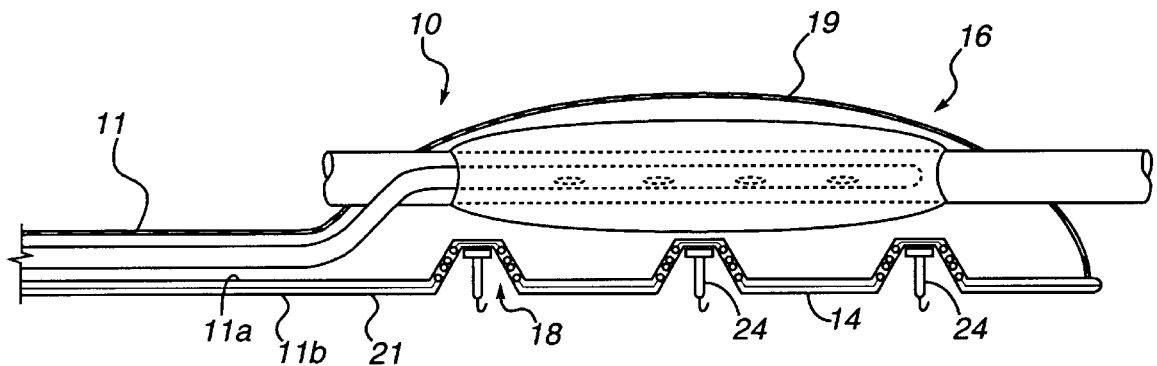
FIG. 3a is a fragmented view of the unsheathed apparatus showing a wire along the tube and stapling surface.
Figure 3B:
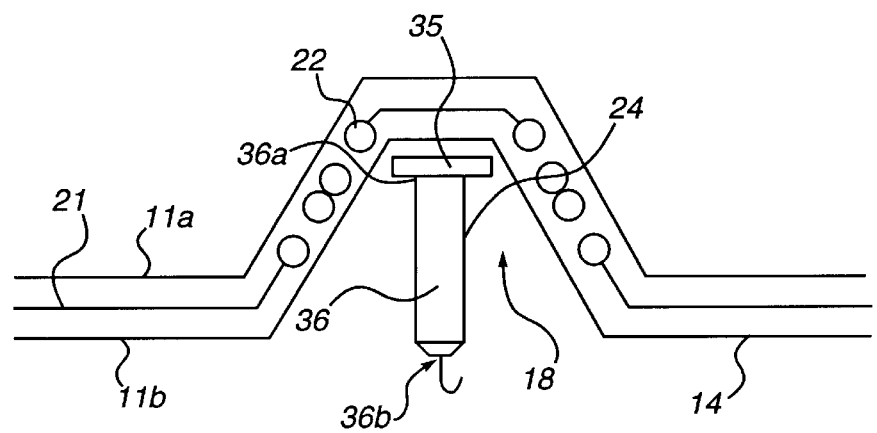
FIG. 3b is a close up view of a capsule of the apparatus loaded with a pin.

As illustrated in FIGS. 3a and 3b, thin conductive wire 21 is embedded between inner surface 11a and outer surface 11b of tube 11 extending along the length of tube 11 and throughout the length of stapling surface 14 of stapling device 16. In particular, wire 21 passes through capsules 18 for the purpose of carrying a magnetic charge therethrough.

Adverting particularly to FIG. 3b, capsules 18 are preferably 1.55 mm wide and 4.25 mm deep in their pre-flexed position. Moreover, each capsule 18 contains at least one miniature electromagnet, preferably coil 22. Coils 22 are in physical communication with wire 21 to hold pins 24 in place prior to and during penetration of graft material and a portion of a vessel wall. In addition, wire 21 is preferably comprised of sufficient turns (~25) of nylon coated subguage wire.

With specific reference to FIG. 3a, apparatus 10 is further comprised of a standard means for applying a magnetic charge to said thin conductive wire 21 and coils 22.

Referring again to FIGS. 1a–1c, balloon catheter 15 is comprised of an inflatable/deflatable balloon 25 at its distal end. Furthermore, balloon catheter 15 is positioned within central lumen 12 of tube 11 with balloon 25 positioned within hollow portion 20 of stapling device 16. Balloon 25 is preferably comprised of a rigid or semi-rigid polyurethane. Moreover, apparatus 10 contains a means for inflating and deflating balloon 25. The most preferred means for inflating and deflating balloon 25 is a syringe (not shown).

Figure 4:
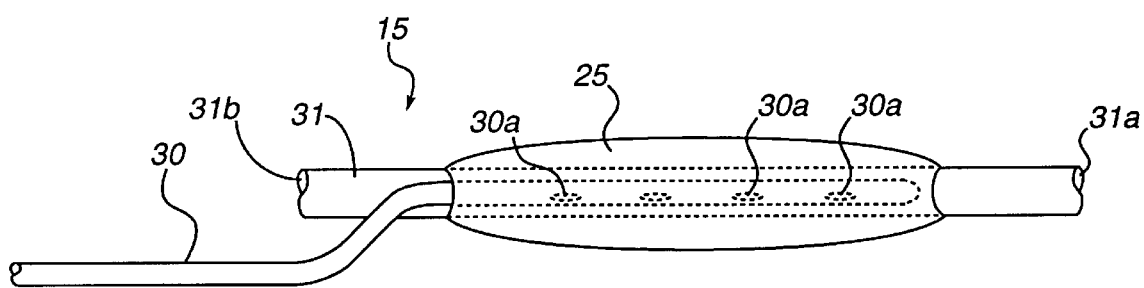
FIG. 4 is a side perspective view of the balloon catheter portion of the apparatus.

As shown in FIG. 4 balloon catheter 15 is additionally comprised of a first lumen 30 in fluid communication with the interior of balloon 25 for use in connection with syringe (not shown) to inflate and deflate balloon 25. Fluid passes through first lumen 30 and into balloon 25 via lumen openings 30a. Furthermore, balloon catheter 15 is comprised of a second lumen 31 passing through the entire length of balloon catheter 15 and having an opening at the proximal end 31a and distal end 31b of balloon catheter 15. Second lumen 31 may be used to pass apparatus 10, and balloon catheter 15 in particular, over a guide wire (not shown) for passage of apparatus 10 through a blood vessel. Second lumen 31 additionally functions to allow passage of blood through a vessel during use of apparatus 10. Second lumen 31 provides a substantially unobstructed path for blood flow during use of apparatus 10.

Figure 5A:
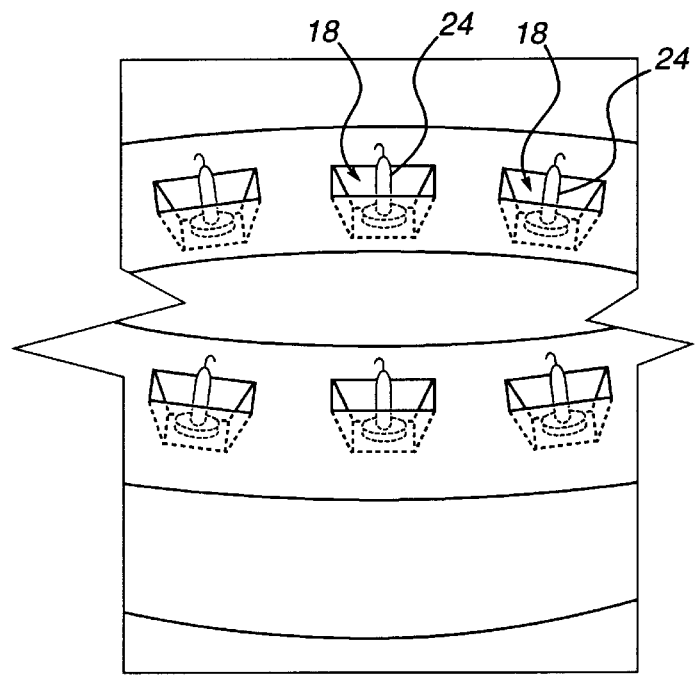
FIG. 5a is a bottom view of a portion of the stapling surface of the apparatus.
Figure 5B:
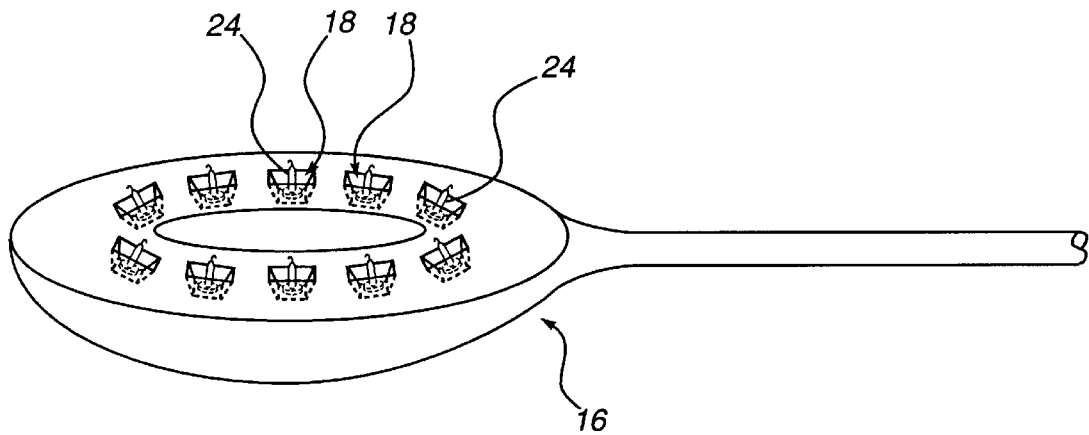
FIG. 5b is a bottom perspective view of the entire stapling surface of the apparatus.

As shown in FIGS. 5a and 5b, one or more pins 24 are placed within capsules 18 prior to insertion. A magnetic charge is applied to wire 21 or coils 22 (shown in FIGS. 3a and 3b) after stapling device 16 is positioned for deployment of pins 24.

Referring now to FIGS. 6a–6e, prior to application of a magnetic charge and during movement through a vessel, pins 24 are held within capsules 18 by sheath 17. Sheath 17 is preferably comprised of top layer 50 and bottom layer 51 with fillable space 52, and terminating in a sealed, stretchable ring 53. Sheath 17 is preferably comprised of PTFE or mylar material. Sheath 17 has the additional function of receiving a fluid such as liquid nitrogen, water, saline, or an inert gas to provide rigidity to the apparatus as it passes through a blood vessel toward a point of deployment. A syringe may be used for adding or removing fluid as needed for rigidity. It is preferable to fill sheath 17 with 2–3 CMS of fluid for adequate maximum rigidity. In particular, sheath is filled by passing fluid through a lumen 60 in communication with fillable space 52 of sheath 17.

When stapling device 16 has been positioned for deployment of pins 24, a magnetic charge is applied to wire 21, preferably 100 mA, 10 V, 50 ohms, and 1 watt of power. Sheath 17 is then retracted and pins 24 are held within capsules 18 by the magnetic charge running through thin conductive wire 21 to magnetic coils 22 within capsules 18.

Referring again to FIG. 3b, pins 24 are of varying length, preferably 4 mm; varying width, preferably 1.5 mm; and comprised of a ferromagnetic material such as, titanium or platinum, and coated with a biocompatible material able to withstand the mechanical stresses associated with insertion. Pins 24 are further comprised of a head 35 and an insertion portion 36. Insertion portion 36 is affixed to head 35 at its proximal end 36a and its distal end 36b is comprised of a hook shape for purposes of maintaining pin 24 in position after penetration of graft material and a blood vessel wall.

As shown in FIGS. 2, as well as FIGS. 6a–6e, capsules 18 as well as stapling surface 14 are preferably comprised of a flexible material such as silicone rubber or polyurethane. Such a flexible material enables the capsules 18, containing pins 24 to flex downward to form a continuum stapling surface 14 and force pins 24 to extend outward from stapling surface 14 and, in use, to penetrate graft material 60 and a blood vessel wall 61.

Figure 6A:
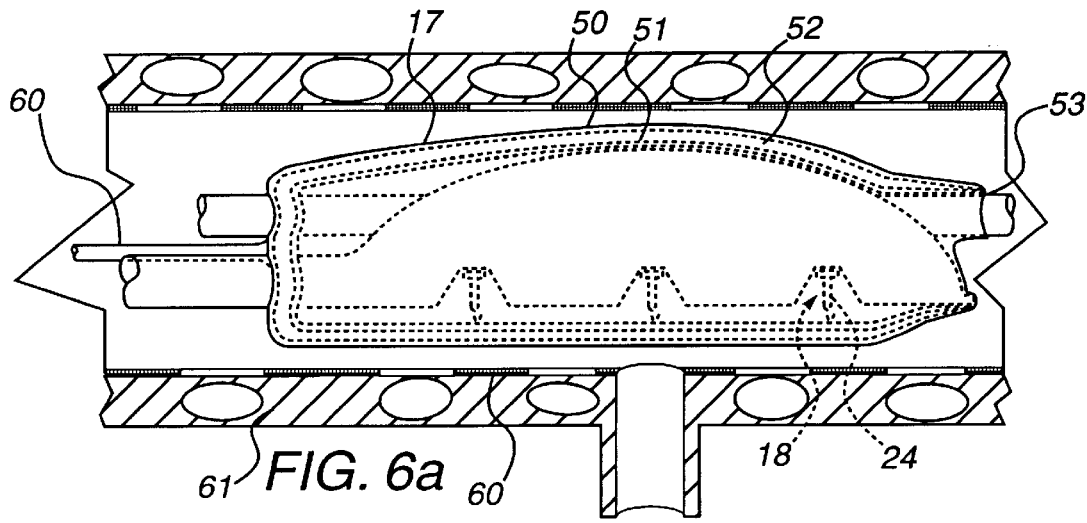
FIG. 6a is a side elevational view of the sheathed apparatus within a blood vessel.
Figure 6B:
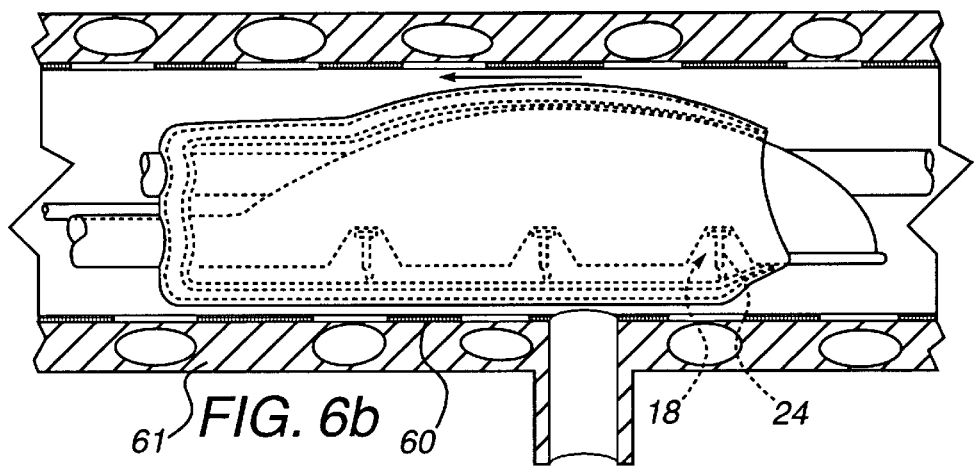
FIG. 6b is a side elevational view of the partially sheathed apparatus within a blood vessel.
Figure 6C:
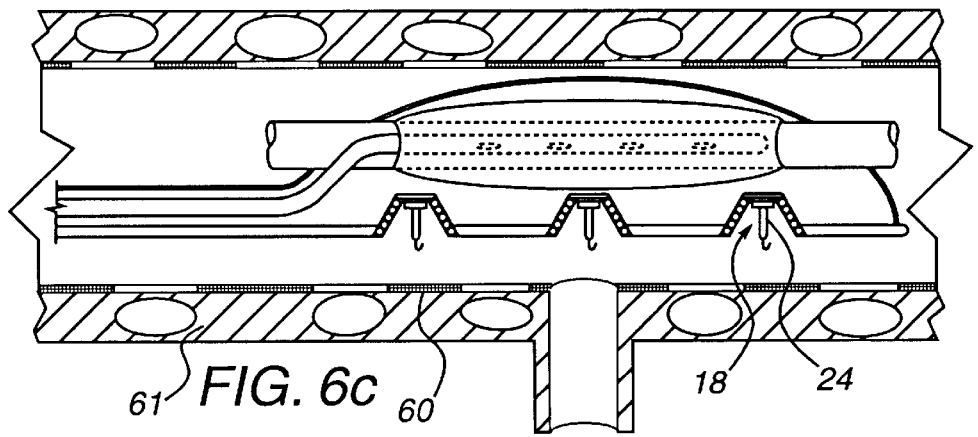
FIG. 6c is a fragmentary view of the unsheathed apparatus within a blood vessel.
Figure 6D:
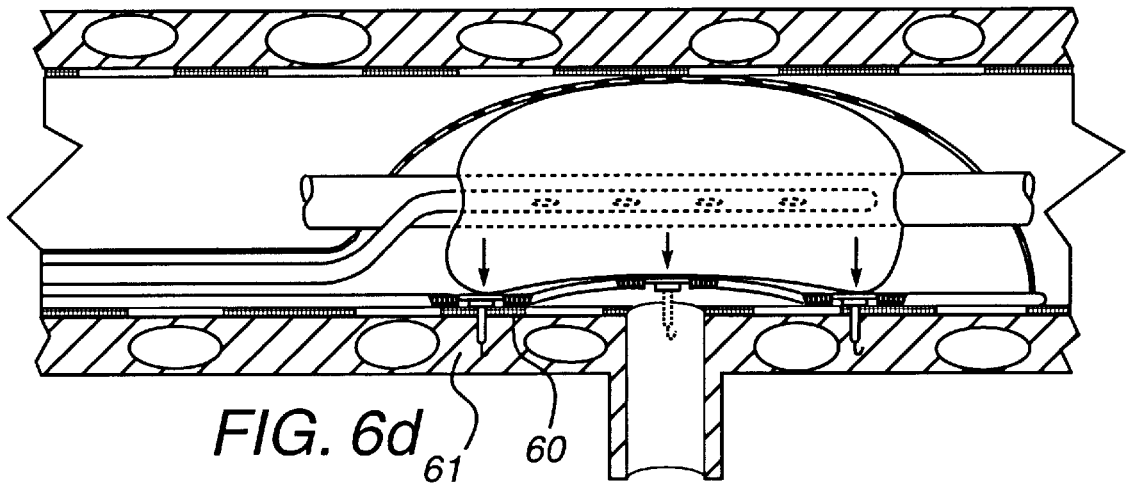
FIG. 6d is a fragmentary view of the unsheathed apparatus within a blood vessel.
Figure 6E:
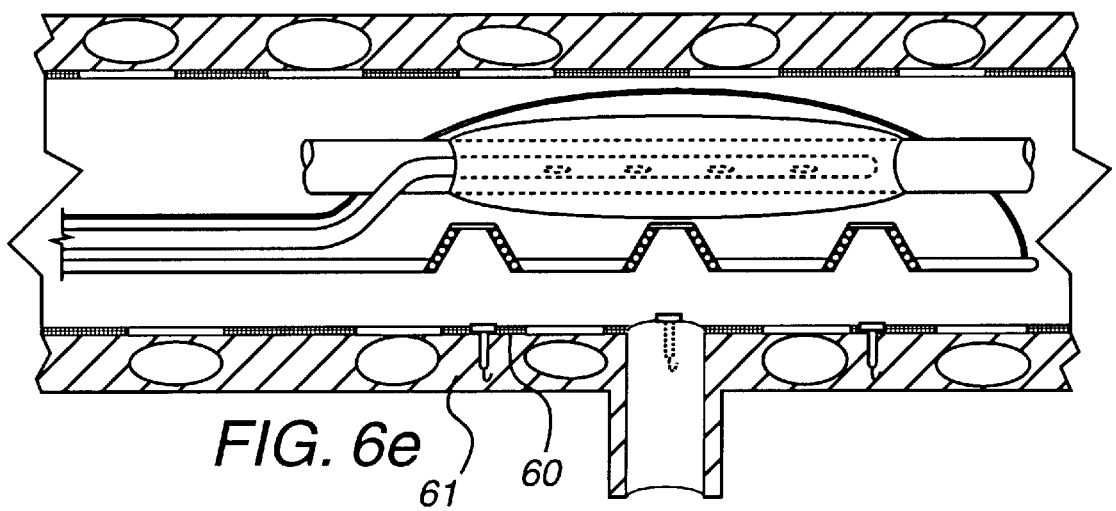
FIG. 6e is a fragmentary view of the unsheathed apparatus within a blood vessel.

As shown further in FIGS. 6a and 6b, sheath 17 is removed by pulling filling lumen 60 which forces ring 53 to stretch over and around stapling device 16 and releasing pins 24.

As shown further in FIGS. 6a–6e, the present invention further comprises a method for stapling graft material against the aortic wall while preserving patency of orifices of branches of the aorta. The inventive method is comprised of the following steps:

(a) presizing the stapling device 16 utilizing the graft opening and size of the blood vessel lumen;

(b) positioning pins within capsules 18 of stapling surface 14 with hook portion 36b extending outward from capsule 18;

(c) placing apparatus within sheath 17 for temporarily retaining pins 24 in position and protecting vessel wall from contact with hook portion 36b of pins 24 during movement of apparatus 10 through a blood vessel;

(d) inserting apparatus 10 into the previously created entry point for deployment of aortic graft and pass apparatus 10 over previously placed guide wire;

(e) move apparatus 10 through blood vessel to the point where stapling device 16 is appropriately placed within the lumen of the deployed aortic graft and such that pins 24 are appropriately positioned to staple graft material to an aortic wall around orifices of branches of the aorta;

(f) filling sheath 17 with fluid for rigidity and removing fluid when a reduced size is necessary during movement of apparatus 10 through the blood vessel;

(g) verify position utilizing standard imagining means;

(h) removing fluid from sheath 17;

(i) energizing electromagnetic coils 22 by applying approximately 100 mA, 10 V, 50 ohms, and 1 watt to thin conductive wire 21 and each coil 22 thereby retaining pins 24 within capsules 18;

(j) removing sheath 17 from the vessel thereby exposing pins 24 to graft material 60 and vessel wall 61;

(k) inflating balloon 25 until upper surface and stapling surface 14 of stapling device 16 have contacted both the upper and lower vessel wall;

(l) de energizing electromagnetic coils 22;

(m) fully deflating balloon 25;

(n) verifying position utilizing standard imaging techniques; and (o) removing apparatus 10 from blood vessel and closing incision utilizing standard technique.

I claim:

1. An apparatus for stapling graft material to a vessel wall comprising in combination:

a stapling device, said stapling device comprising an expandable member and a tube, said tube having a proximal end and a central lumen, said expandable member being integrally connected to said proximal end of said tube, said expandable member further having an upper surface and a stapling surface which are integrally connected to define a closed, substantially hollow structure, said hollow structure communicating with said central lumen of said tube;

a balloon catheter, said balloon catheter being configured for insertion through said central lumen of said tube and into said expandable member for activation of said stapling device; and an inflation means for inflating said balloon catheter.

2. An apparatus according to claim 1 wherein said stapling surface comprises one or more capsules; a magnetic coil within each capsule; and a means for applying and releasing a magnetic charge to said coil.

3. An apparatus according to claim 2 wherein said means for applying and releasing a magnetic charge to said coil comprises a conductive wire in contact with said magnetic coils within each capsule.

4. An apparatus according to claim 3 wherein said tube further comprises an inner surface and an outer surface, and said wire passes between said inner surface and said outer surface.

5. An apparatus according to claim 2 further comprising one or more pins positioned within each capsule.

6. An apparatus according to claim 5 wherein said one or more pins are comprised of a head and insertion portion; said insertion portion having a proximal and distal end; said proximal end of said insertion portion integral with said head; said distal end of said insertion portion in a hook shape for affixing said pin in position after deployment.

7. An apparatus according to claim 1 wherein said upper surface is stretchable.

8. An apparatus according to claim 1 wherein said balloon catheter comprises a proximal end, an inflatable/deflatable balloon integral with said proximal end, a first lumen for passing said balloon catheter over a guide wire, and a second lumen in fluid communication with said balloon.

9. An apparatus according to claim 1 where said inflation means is a syringe.

10. An apparatus according to claim 1 further comprising a sheath.

11. An apparatus according to claim 10 wherein said sheath is retractable.

12. An apparatus according to claim 11 wherein said sheath is comprised of a fillable space and a ring.

* * * * *